(12) United States Patent
Cao et al.

(10) Patent No.: US 11,805,783 B2
(45) Date of Patent: Nov. 7, 2023

(54) GROWTH-PROMOTING BACTERIAL AGENT CAPABLE OF IMPROVING CONTENT OF SOYBEAN OIL, PREPARATION METHOD AND USE THEREOF

(71) Applicant: ANHUI AGRICULTURAL UNIVERSITY, Anhui (CN)

(72) Inventors: Yuanyuan Cao, Hefei (CN); Wenfeng Al, Hefei (CN); Quande Li, Hefei (CN); Tingting Guo, Hefei (CN); Kangmiao Ou, Hefei (CN); Ke Cai, Hefei (CN); Lijuan Qiu, Hefei (CN); Xiaobo Wang, Hefei (CN); Jia Liu, Hefei (CN); Yunyu Li, Hefei (CN); Xin Ruan, Hefei (CN); Yuanyuan Xue, Hefei (CN); Yubei Huo, Hefei (CN); Ruining Deng, Hefei (CN)

(73) Assignee: ANHUI AGRICULTURAL UNIVERSITY, Hefei (CN)

( * ) Notice: Subject to any disclaimer, the term of this patent is extended or adjusted under 35 U.S.C. 154(b) by 0 days.

(21) Appl. No.: 17/822,763

(22) Filed: Aug. 26, 2022

(65) Prior Publication Data
US 2023/0080419 A1 Mar. 16, 2023

(30) Foreign Application Priority Data
Aug. 26, 2021 (CN) .......................... 202110986247.5

(51) Int. Cl.
*A01N 63/22* (2020.01)
*A01C 1/06* (2006.01)
*A01C 21/00* (2006.01)
*C12N 1/20* (2006.01)

(52) U.S. Cl.
CPC ................ *A01N 63/22* (2020.01); *A01C 1/06* (2013.01); *A01C 21/00* (2013.01); *C12N 1/20* (2013.01)

(58) Field of Classification Search
CPC .......... A01C 1/06; A01C 21/00; A01N 63/22; C12N 1/20
See application file for complete search history.

(56) References Cited

FOREIGN PATENT DOCUMENTS

| CN | 109136153 A | 1/2019 |
| CN | 109652340 A | 4/2019 |
| CN | 111100818 A | 5/2020 |
| CN | 111154675 A | 5/2020 |
| CN | 112111427 A | 12/2020 |

OTHER PUBLICATIONS

Decision to grant a patent in Chinese Application No. 202110986247.5 dated Jul. 25, 2022, 5 pages.

*Primary Examiner* — Ali Soroush
(74) *Attorney, Agent, or Firm* — METIS IP LLC

(57) ABSTRACT

A growth-promoting bacterial agent capable of improving content of soybean oil, preparation method, and use thereof are provided. The growth-promoting bacterial agent is fermented by a DW1 strain, the classification name of the DW1 strain is *Bacillus* sp., the DW1 strain is deposited in the China Center for Type Culture Collection on Jul. 16, 2021, and the deposit number is CCTCC NO: M 2021889. The growth-promoting bacterial agent of the present disclosure has the ability to dissolve insoluble phosphorus and insoluble potassium and can increase content of readily available phosphorus and readily available potassium in the soil, which has an obvious promoting effect on the growth of soybean and improves soybean yield. The growth-promoting bacterial agent of the present disclosure promotes bacteria and can significantly improve the content of soybean oil. At the same time, it has an affinity of soybean agglutinin and can agglutinate with the soybean agglutinin.

5 Claims, 2 Drawing Sheets
Specification includes a Sequence Listing.

GROWTH-PROMOTING BACTERIAL AGENT CAPABLE OF IMPROVING CONTENT OF SOYBEAN OIL, PREPARATION METHOD AND USE THEREOF

CROSS-REFERENCE TO RELATED APPLICATIONS

This application claims priority of Chinese Patent Application No. CN202110986247.5, filed on Aug. 26, 2021; the entire contents of which are incorporated herein by reference.

SEQUENCE LISTING

The instant application contains a Sequence Listing which has been submitted electronically in XML format and is hereby incorporated by reference in its entirety. The XML copy, created on Aug. 23, 2022, is named "Sequence Listing-61801-0002US00" and is 3,254 bytes in size.

TECHNICAL FIELD

The present disclosure relates to the field of microbiological technology, and in particular, to a growth-promoting bacterial agent for soybean capable of improving soybean yield and content of the soybean oil and dissolving phosphorus and potassium, and a preparation method and use thereof.

BACKGROUND

Soybean is an important grain and oil crop in China, which provides a large number of raw materials for agriculture and industry. Phosphorus and potassium are of great significance to soybean yield and soybean quality. Phosphorus participates in important life activities such as photosynthesis, respiration, and the like of the soybean, and phosphorus deficiency leads to the slow growth, the yellowing of leaves, and the delay of the flowering phase and the mature phase of the soybean. Potassium can activate a plurality of enzyme activities in cells, participate in maintaining osmotic pressure balance of plant cells, enhance stress resistance of plants such as cold resistance, salt resistance, and lodging resistance, and improve $CO_2$ assimilation rate, promoting photosynthesis of plants. In order to improve the soybean yield, people use a large amount of phosphate fertilizers and potassium fertilizers in the soybean planting process, but a large amount of phosphate fertilizers and potassium fertilizers enter farmlands and react with metal ions such as zinc and the like to generate insoluble compounds, so that soil is hardened, and the soil quality is reduced.

Soybean oil is rich in fatty acids necessary for the human body, which can reduce cholesterol content in the human body, and has good health functions. At the same time, the soybean oil is also a renewable biological energy source and is an important biofuel source second to alcohol, so the method for improving the content of the soybean oil has high economic value in terms of food health and industrial raw materials.

As a huge phosphorus and potassium library, the soil has the high total content of phosphorus and potassium, but most of the phosphorus and potassium exist in the form of insoluble compounds that are difficult for plants to absorb and use, and it is difficult to meet the high-yield needs of crops. There is a kind of plant growth promoting rhizobacteria in the soil, which can dissolve insoluble phosphorus and insoluble potassium, improve the content of readily available phosphorus and readily available potassium in the soil, supply them to plants, and promote plant growth and development. Therefore, the development of the microbial fertilizer bacteria agent by using the plant growth promoting rhizobacteria is an effective way of promoting the absorption of soybean nutrients, improving soybean yield, and reducing the application number of fertilizers. The common microbial fertilizer bacteria agent can only provide nutrient elements required by soybean growth, cannot improve the important quality index of soybean oil content at the same time, and cannot ensure that a strain can survive for a long time and can play a stable beneficial function at the plant rhizosphere. Therefore, the growth-promoting bacterial agent for soybean, which is specifically compatible with the soybeans and can stably colonize, is developed to promote nutrient absorption and oil accumulation of the soybean, improve soybean yield and soybean quality, change the traditional fertilization mode, improve the agricultural income, accord with the health development concept of modern agriculture, and have profound significance on the sustainable development of green agriculture.

SUMMARY

In order to solve the problems existing in the prior art, one of the purposes of the present disclosure is to provide a growth-promoting bacterial agent for soybeans.

The growth-promoting bacterial agent is fermented by a DW1 strain, the classification name of the DW1 strain is *Bacillus* sp., the DW1 strain is deposited in the China Center for Type Culture Collection on Jul. 16, 2021, the preservation address is Luojia mountain, Bayi Road, Wuchang District, Wuhan City, Hubei Province, and the deposit number is CCTCC NO: M 2021889.

Preferably, the growth-promoting bacterial agent is a liquid bacterial agent.

Preferably, the application amount of the liquid bacterial agent per hectare of soybean fields is 10-50 L, and a count of living bacteria in the liquid bacterial agent is within the range of $1\times10^8$–$9\times10^8$ CFU·mL$^{-1}$.

The second purpose of the present disclosure is to provide preparation method of the growth-promoting bacterial agent for soybeans. The preparation method is as follows:

S1. activating the DW1 strain, which includes inoculating the DW1 strain into an LB slope medium, and culturing the DW1 strain at 25-30° C. for 18-30 h;

S2. culturing the DW1 strain in a liquid medium, which includes washing the DW1 strain on the LB slop medium with physiological saline, inoculating the DW1 strain into 80-120 mL of the LB liquid medium with a volume ratio of 2-5%, placing the strain in a shaker at 25-30° C., 120-180 r·min$^{-1}$ for shaking cultivation for 24-28 h to prepare the liquid bacterial agent.

The third purpose of the present disclosure is to provide a use of the above-mentioned growth-promoting bacterial agent for soybeans, the growth-promoting agent is used for at least one of seed soaking, coating, or root watering of soybeans.

The present disclosure has the following beneficial effect.

1. The growth-promoting bacterial agent of the present disclosure significantly promotes soybean growth, which can significantly increase the amount of phosphorus and potassium content of soybean leaves, and can improve soybean yield. The root of soybeans can produce soybean agglutinin, which is a protein or a glycoprotein of non-immunological origin that bind to polysaccharides on the bacterial cell wall. The strain of the present disclosure has an affinity of soybean agglutinin and can agglutinate with the soybean agglutinin. The DW1 strain is colonized on the root of the soybean for a long time under the mediation of the soybean agglutinin, providing the stable effect of growth-promoting.

2. The DW1 strain of the present disclosure has the ability to dissolve insoluble phosphorus and insoluble potassium and can increase content of readily available phosphorus and readily available potassium in the soil.

The phosphorus dissolving mechanism of the DW1 strain is mainly as follows: 1) the strain secretes organic acids such as acetic acid, malic acid, citric acid, etc., in the metabolic process, reduces the pH value of soil, and chelates with $Fe^{3+}$ $Al^{3+}$ $Ca^{2+}$ ion, etc., thereby dissolving insoluble inorganic phosphates; 2) $CO_2$ released by respiration of the strain can reduce the pH value of the environment, thereby dissolving the insoluble inorganic phosphates.

The potassium dissolving mechanism of the DW1 strain is mainly as follows: 1) the strain secretes organic acids such as oxalic acid, tartaric acid, acetic acid, citric acid, and dissolving insoluble potassium; 2) the DW1 strain contacts with minerals to generate special enzymes which destroy the crystal structure of ores in soil and generate ion exchange reaction to release potassium in the soil; 3) the extracellular polysaccharide secreted by the DW1 strain can tightly wrap the mineral so that the bacteria can be tightly contacted with the ore, the concentration of organic acid on the surface of the mineral is improved, and potassium in the mineral is released under the combined action of the acid dissolution and complexation of the organic acid; 4) the DW1 strain forms a bacterial mineral complex with secreted extracellular polysaccharide and potassium feldspar, the strain generates corrosion action on the fragile part of the surface of mineral particles, and metabolite generated by the strain performs chemical degradation action on minerals to release potassium ions and the like, so that insoluble potassium is converted into soluble readily available potassium for soybean absorption.

3. The DW1 strain of the present disclosure also has the ability to produce indole-3-acetic acid (IAA). Indole-3-acetic acid is an important auxin and can regulate and promote the growth of plant buds, stems and roots, and influence the establishment of plant organs.

4. The DW1 growth-promoting bacteria agent of the present disclosure can obviously improve the nitrogen content, the phosphorus content and the potassium content of soybean leaves, obviously improve the number of seeds per plant, the weight of beans per plant, and the weight of 100 seeds, and obviously improve the oil content of the soybean, and obviously promote the growth of the soybean, thereby improving soybean yield and soybean quality, and increasing the income.

5. The DW1 bacteria agent of the present disclosure is applied to the soil with the dosage of 10-50 L/hm². At present, when soybean is planted, the application amount of phosphorus fertilizer is about 90 kg/hm², and the application amount of potassium fertilizer is about 120 kg/hm². In contrast, the use of a growth-promoting bacteria agent provided by the present disclosure can reduce the application amount of phosphorus fertilizer and potassium fertilizer, relieve soil hardening and save energy consumption, and has wide application prospect.

DETAILED DESCRIPTION

Figure 1:
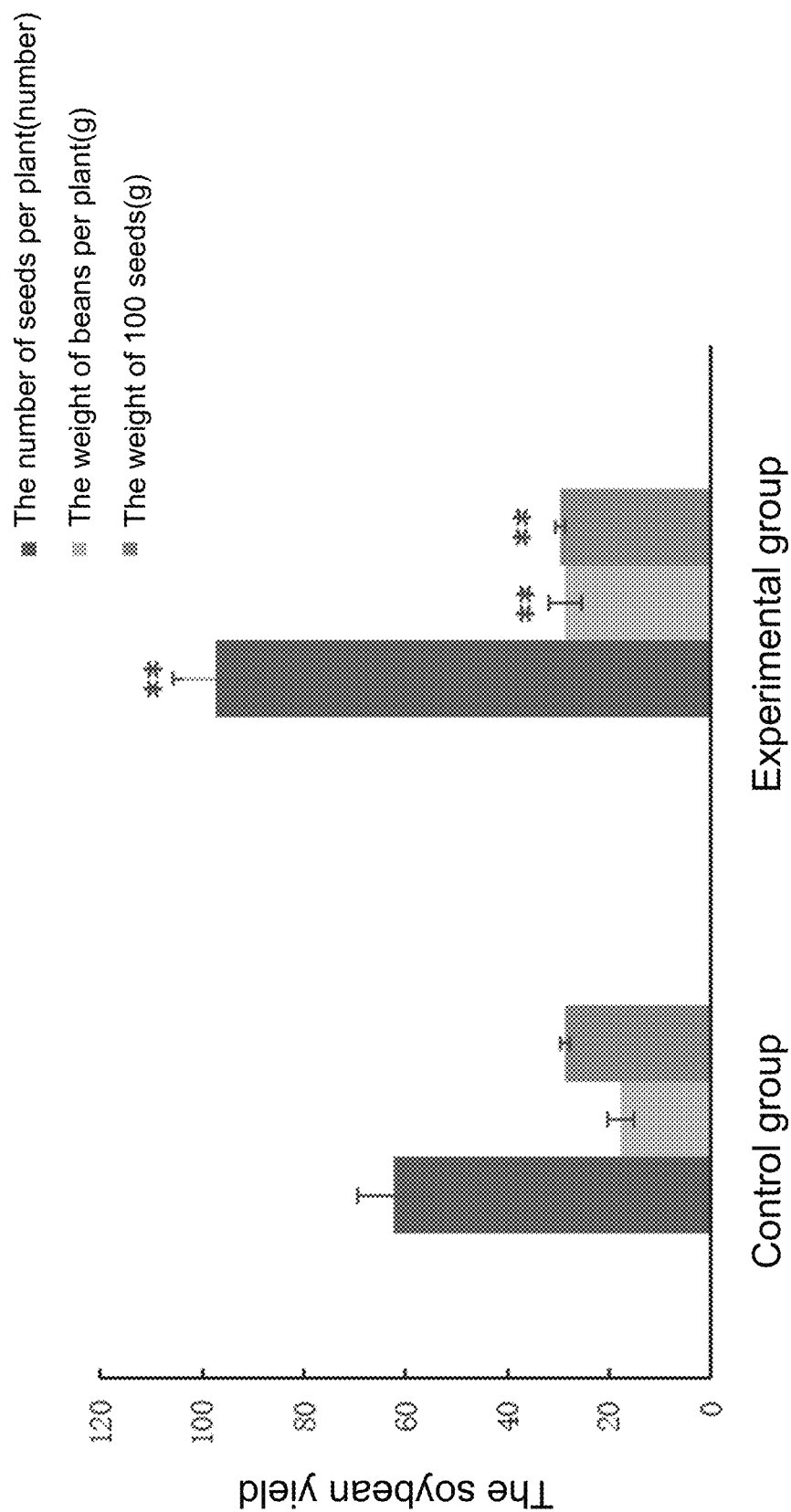
FIG. 1 shows the influence of the DW1 bacteria agent provided by the present disclosure on soybean yield in field tests.

The following embodiments are further described by the present disclosure.

Embodiment 1

Strain Screening

Strong soybean plants were selected as samples, the roots of the soybean plants with soil were dug out, larger soil blocks and other useless residues were removed, 1 g of rhizosphere soil of each sample were took respectively to sterile physiological saline containing nystatin, and placed in a shaker for oscillating at 160 r·min⁻¹ for 0.5 h to obtain rhizosphere soil bacterial suspension. 1 mL of the above-mentioned bacterial suspension was took to 9 mL of sterile physiological saline containing nystatin, and gradient diluted to $10^{-7}$ concentration. The above-mentioned bacterial suspension was coated on a phosphate-dissolving and potassium-dissolving solid medium containing nystatin, repeated 3 times at each concentration, and cultured at the constant temperature of 28° C. for more than 3 days until a transparent ring appears.

The formula of the above phosphate-dissolving solid medium is as follows: glucose 10 g, $K_2HPO_4$ 2.0 g, ammonium sulfate 0.5 g, NaCl 0.3 g, KCl 0.3 g, $MgSO_4 \cdot 7H_2O$ 0.3 g, $FeSO_4 \cdot 7H_2O$ 0.03 g, $MnSO_4 \cdot 4H_2O$ 0.03 g, $Ca_3(PO_4)_2$ 10 g, agar 15 g, distilled water 1000 mL, pH 7.2.

The formula of the potassium-dissolving solid medium is as follows: $Na_2HPO_4$ 2.0 g, $MgSO_4 \cdot 7H_2O$ 0.5 g, $FeCl_3$ 0.005 g, $CaCO_3$ 0.1 g, potassium feldspar 1.0 g, sucrose 5.0 g, agar 15 g, and distilled water 1000 mL, pH 7.0-7.5.

The diameter H of the transparent ring and the diameter C of a colony were observed and measured and the ratio of the two (H/C) was calculated. The strain with the larger H/C value has stronger phosphorus or potassium dissolving capacity.

The colonies with transparent rings were picked to the LB medium containing 50 mg·L⁻¹ nystatin, then streaked and purified a plurality of times to obtain a pure growth-promoting strain. The LB medium formula is peptone 10 g, yeast powder 5 g, NaCl 10 g, agar 15 g, and distilled water 1000 mL.

The growth-promoting strains obtained by screening were inoculated in LB liquid medium, shaked cultivation at constant temperature for 1 day to logarithmic phase, packaged the medium in a centrifuge tube, centrifuged at 3000 r·min⁻¹ for 10 min, and collected bacteria. The bacteria were putted into sterile water, the bacteria were blowed and sucked for a plurality of times by using a pipettor to disperse and suspend the bacteria, centrifuged and washed the bacteria, and repeated the steps 3 times to obtain the bacterial suspension. If the liquid is turbid by observation, a small amount of sterile water was added for dilution. 25 μL of the bacterial suspension were dripped to the center of the glass slide, mixed with soybean agglutinin of equal volume, stood at room temperature for 0.5 h, dried, and the reaction was observed under a microscope after dyeing.

The strains with agglutination reaction were picked to obtain soybean affinity growth-promoting strains. The DW1 applied for the present disclosure is the growth-promoting strain with soybean affinity obtained by the screening method.

Embodiment 2

Determination of Growth-Promoting Ability of the DW1 Strain

A double screening method of a selective medium and soybean agglutinin were adopted to screen growth-promoting bacteria with specific affinity with soybeans from the soybean rhizosphere, and the phosphorus-dissolving, potassium-dissolving, and IAA-producing abilities of the strains were determined. Bacterial suspension was prepared from the strain, inoculated to different phosphate-dissolving and potassium-dissolving mediums, and shaked for cultivation at 28° C. and 160 r·min$^{-1}$ for 5 days.

The formula of the phosphate-dissolving medium is the same as the embodiment 1, which only removes the agar; determining the soluble phosphorus content in each culture solution by a Mo—Sb Anti-Spectrophotometry Method.

The formula of the potassium-dissolving solid medium is as follows: $Na_2HPO_4$ 2.0 g, $MgSO_4.7H_2O$ 0.5 g, $FeCl_3$ 0.005 g, $CaCO_3$ 0.1 g, potassium feldspar 1.0 g, glucose 5.0 g, and distilled water 1000 mL, pH 7.0-7.5. Shaking cultivation was performed at 28° C. and 160 r·min$^{-1}$ for 5 days. 4 mL of $H_2O_2$ were added to each bottle of the bacterial solution, which was digested at 121° C. for 30 min and then centrifuged at 6000 r·min$^{-1}$ for 5 min, supernatant was took to make up to 100 mL, and the content of readily available potassium in the supernatant was determined by adopting a flame photometer.

Compared with the phosphorus-dissolving and potassium-dissolving abilities of various strains, the DW1 strain has stronger phosphorus-dissolving and potassium-dissolving abilities and better dissolving abilities on insoluble phosphorus and insoluble potassium.

IAA production ability of the selected DW1 strain was determined. The DW1 strain was inoculated into a nitrogen-containing liquid medium for shaking cultivation at 28° C. and 160 r·min$^{-1}$ for 5 days, centrifuged to remove precipitation, supernatant was collected, corresponding Sackowski's chromogenic reagent was added to the supernatant according to a ratio of 1:2, mixed and reacted at 25° C. in dark for 30 min. A nitrogen-containing liquid medium without strain inoculation was used as a blank control, absorbance at 530 nm was determined and thus, calculated IAA production level of the DW1 strain was calculated.

Sackowski's chromogenic reagent: 1 mL of 0.5 mol·L$^{-1}$$FeCl_3$ solution is added to 50 mL of 35% $HClO_4$ solution and mixed evenly. The formula of the nitrogen-containing liquid medium is as follows: sucrose 10.0 g, $K_2HPO_4$ 2.0 g, $MgSO_4.7H_2O$ 0.5 g, NaCl 0.1 g, yeast extract 0.5 g, $CaCO_3$ 0.5 g, agar 20 g, distilled water 400 mL, pH 7.0.

The phosphorus-dissolving and potassium-dissolving abilities and the IAA production ability of the DW1 strain are shown in Table 1. As can be seen from Table 1, the DW1 strain has a strong dissolving ability to insoluble phosphorus and insoluble potassium and has a high IAA production ability, indicating that the DW1 strain has the potential of promoting plant growth.

TABLE 1

The phosphorus-dissolving and potassium-dissolving abilities and the IAA production ability of the DW1 strain

| Strain | Phosphorus-dissolving ability (mg · L$^{-1}$) | Potassium-dissolving ability (mg · L$^{-1}$) | IAA production ability (mg · L$^{-1}$) |
|---|---|---|---|
| DW1 | 156.23 ± 9.36 | 10.73 ± 1.54 | 80.50 ± 3.01 |

Embodiment 3

Identification of Strains

A strain specie of the DW1 strain was identified by combining morphological observation, physiological and biochemical tests, and 16SrRNA gene sequence alignment analysis.

Physiological and biochemical characteristics of the DW1 strain were detected according to "Common Bacterial System Appraisal Manual" and "Berje's Bacterial Appraisal Manual". The morphological test comprises gram staining; the physiological and biochemical tests comprise starch hydrolysis test, catalase test, VP test, methyl red (M-R) test, gelatin liquefaction test, glucose oxidation-fermentation test, and $H_2S$ production test, the results are shown in Table 2.

The 16SrRNA gene sequence of the DW1 strain was submitted to the NCBI database for BLAST comparison, the DW1 strain is determined to belong to the *Bacillus* sp. according to the results of the physiological and biochemical tests, and the 16SrRNA gene sequence of the DW1 strain is shown in SEQ ID NO. 1 listed in the Sequence List file.

TABLE 2

Some physiological and biochemical characteristics of the DW1 strain

| Strain | Starch hydrolysis | Catalase | VP | M-R | Gelatin liquefaction | Glucose oxidation-fermentation | $H_2S$ production | Gram staining |
|---|---|---|---|---|---|---|---|---|
| DW1 | + | + | + | — | + | oxidation | — | + |

Embodiment 4

Preparation of the DW1 Growth-Promoting Bacterial Agent and use Thereof in Field Tests of Soybeans 1. Preparation of Bacterial Agent The strain on the LB slop medium was washed with 5 mL of physiological saline, the DW1 strain was inoculated into the LB liquid medium with a volume ratio of 2% for shaking cultivation at 28° C., 160 r·min$^{-1}$ for 24 h to prepare the DW1 liquid bacterial agent. When in use, the bacterial agent was diluted to $OD_{680}$=0.8 by water.

2. Field Tests of the Bacterial Agent

The test is divided into two groups, one group is an experimental group applied with the DW1 bacterial agent and the other group is a control group without a bacterial agent. There are 10 repetitions in each group. Soybean seeds were sowed in the field, and 20 mL of diluted bacterial agent were inoculated to the roots after the soybean seedlings emerge. After the soybeans are mature, the plant height, the node number, the effective branch number, the number of seeds per plant, the weight of beans per plant, and the weight of 100 seeds, the nitrogen content of soybean leaves, the phosphorus content of soybean leaves, the potassium content of soybean leaves, the soil ammonium nitrogen content, the soil effective phosphorus content and the soil readily available potassium content of the experimental group and the control group were determined. The results are shown in FIG. 1, Table 3, Table 4, and Table 5.

TABLE 3

The effect of the DW1 bacterial agent on the growth of soybeans in the field tests

| Treatment | Plant height cm | Node number | Effective branch number |
|---|---|---|---|
| Control group | 43.32 ± 5.07 | 11.81 ± 1.28 | 4.90 ± 0.96 |
| Experimental group | 46.41 ± 3.39 | 12.83 ± 0.72 | 6.14 ± 0.59* |

Note:
*indicates significant differences between treatments ($p < 0.05$).

As can be seen from Table 3, the effective branch number of the experimental group applied with the DW1 bacterial agent is improved by 25.31% compared with the control group without a bacterial agent and reached a significant level ($p<0.05$).

The influence of the DW1 bacterial agent on the soybean yield is shown in FIG. 1, and the number of seeds per plant, the weight of beans per plant, and the weight of 100 seeds of an experimental group applied with the DW1 bacterial agent are respectively improved by 50.82%, 57.83%, and 4.62% compared with a control group without a bacterial agent and reached extremely significant levels ($p<0.01$).

TABLE 4

The effect of the DW1 bacterial agent on the nutrient content of soybean leaves in the field tests

| Treatment | Nitrogen content of the leaves g · kg$^{-1}$ | Phosphorus content of the leaves g · kg$^{-1}$ | Potassium content of the leaves g · kg$^{-1}$ |
|---|---|---|---|
| Control group | 3.99 ± 0.91 | 3.17 ± 0.09 | 10.56 ± 0.57 |
| Experimental group | 6.43 ± 1.08* | 5.22 ± 0.48* | 11.94 ± 0.27* |

Note:
*indicates significant differences between treatments ($p < 0.05$).

As can be seen from Table 4, the nitrogen content, phosphorus content, and potassium content of the leaves of the soybean plants in the experimental group applied with the DW1 bacterial agent are respectively improved by 61.15%, 64.67%, and 13.07% compared with a control group without a bacterial agent, and all reached significant levels ($p<0.05$).

TABLE 5

The effect of the DW1 bacterial agent on soil nutrient content of soybean rhizosphere in the field tests

| Treatment | Ammonium nitrogen content of soil mg · kg$^{-1}$ | Available phosphorus content of soil mg · kg$^{-1}$ | Readily available potassium content of soil mg · kg$^{-1}$ |
|---|---|---|---|
| Control group | 8.07 ± 0.24 | 24.68 ± 3.27 | 110.00 ± 8.00 |
| Experimental group | 12.79 ± 1.18** | 32.50 ± 1.11* | 138.00 ± 13.45* |

Note:
*indicates significant differences between treatments ($p < 0.05$),
**indicates extremely significant difference between treatments ($p < 0.01$).

As can be seen from Table 5, the ammonium nitrogen content, available phosphorus content, and readily available potassium content of rhizosphere soil in the treatment group applied with the DW1 bacterial agent are respectively improved by 58.49%, 31.69%, and 25.45% compared with a control group without a bacterial agent, the improved amount of the soil ammonium nitrogen reached an extremely significant level ($p<0.01$), and the improved amount of soil available phosphorus and soil readily available potassium reached a significant level ($p<0.05$). The DW1 bacterial agent can improve the content of ammonium nitrogen, available phosphorus, and readily available potassium in the soybean rhizosphere soil.

Test group 1 is applied with the DW1 bacterial agent, test group 2 is applied with an FK19 bacterial agent, the control group is applied without a bacterial agent, and there are 10 repetitions in each group. Soybean seeds were sowed in the field, and 20 mL of diluted DW1 bacterial agent and diluted FK19 bacterial agent were inoculated respectively to the roots after the soybean seedlings emerge. The oil content and protein content of the experimental group and the control group were determined; the results are shown in FIG. 2.

The FK19 bacterial agent is prepared from *bacillus* FK19 and has the same growth-promoting effect on soybean, and Chinese invention patent CN 109652340B describes the growth-promoting function of the FK19 bacterial agent on soybean. As can be seen from FIG. 2, the oil content of the soybeans applied with the DW1 bacterial agent is improved by 5.23% compared with the control without the bacterial agent and reached an extremely significant level ($p<0.01$), and the content of the soybean protein is not reduced.

Compared with the control group, the FK19 bacterial agent, which also has the soybean growth-promoting effect, does not show the ability to improve the oil content of soybean. It shows that the DW1 bacterial agent in the present disclosure can improve the oil content of soybean.

Figure 2:
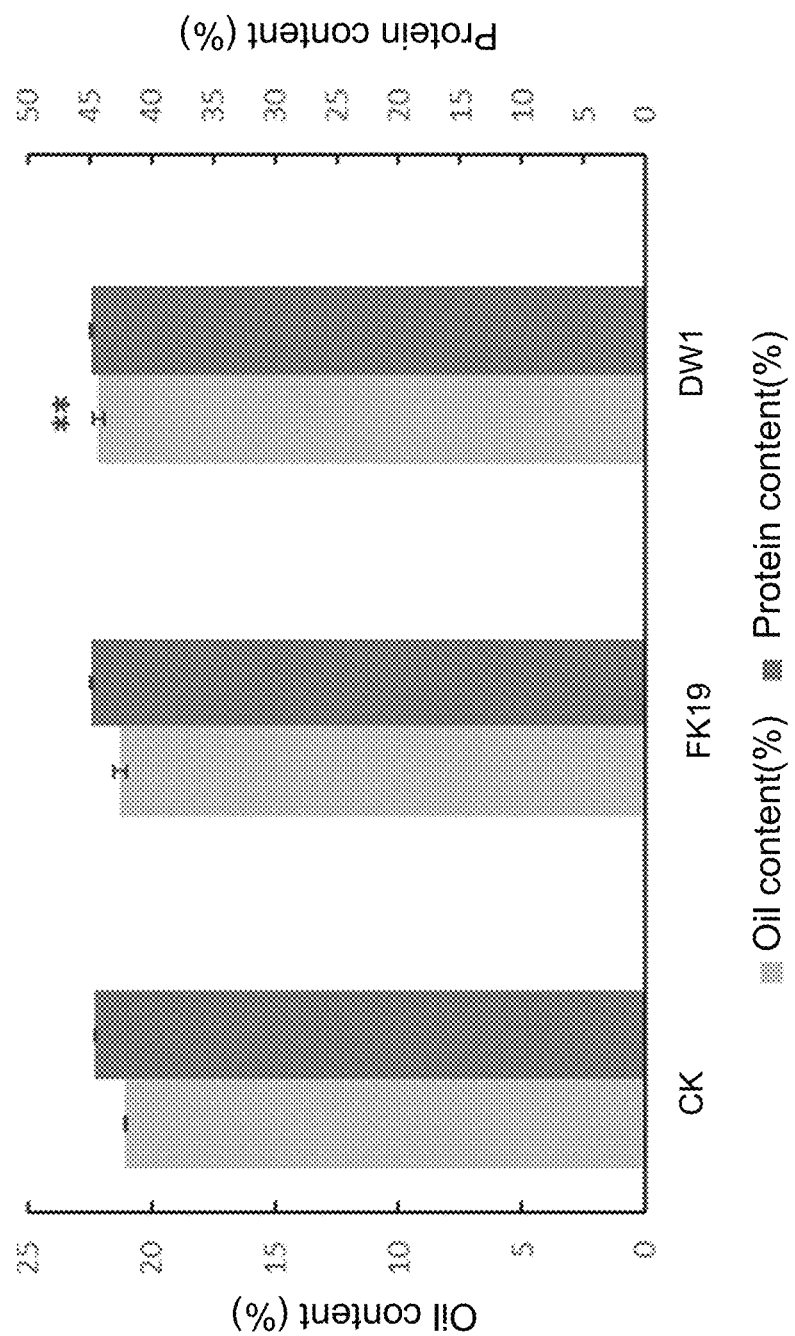
FIG. 2 shows the influence of the DW1 bacteria agent provided by the present disclosure on the oil content and protein content of soybean in field tests.

As can be seen from Tables 3, 4, 5, and FIGS. 1 and 2, the DW1 strain can release insoluble phosphorus and insoluble potassium in the soil, improve the soil soluble nutrient content to promote the absorption of nutrients by soybeans, and improve the nutrient content of soybean leaves, further promote the growth of soybeans, and improve soybean yield and the oil content of the soybean.

It should be emphasized that the growth-promoting bacterial agent provided by the present disclosure can be combined with other bacteria agents or products with growth-promoting effects; although the growth-promoting bacterial agent of the present disclosure uses soybean as the experimental object, the implementation of the growth-promoting bacterial agent containing the DW1 strain on other plants should be regarded as an embodiment of the present disclosure.

The above description is only the preferred embodiments of the present disclosure and is not intended to limit the present disclosure. Although the present disclosure has been described in detail with reference to the foregoing embodiments, those skilled in the art can still modify the technical solutions described in the foregoing embodiments, or equivalently replace some of the technical features. In the spirit and principles of the present disclosure, any modification, equivalent replacement, and improvement of the present disclosure shall be included in the protection scope of the present disclosure.

---

---

What is claimed is:

1. A growth-promoting bacterial agent for soybeans, wherein the growth-promoting bacterial agent is obtained by culturing a DW1 strain in an LB medium, the classification name of the DW1 strain is *Bacillus* sp., the DW1 strain is deposited in the China Center for Type Culture Collection on Jul. 16, 2021, and the deposit number is CCTCC NO: M 2021889.

2. The growth-promoting bacterial agent for soybeans according to claim 1, wherein the growth-promoting bacterial agent is a liquid bacterial agent, which is prepared by culturing the DW1 strain in an LB liquid medium.

3. The growth-promoting bacterial agent for soybeans according to claim 2, wherein the application amount of the liquid bacterial agent per hectare of soybean fields is 10-50 L, and a count of living bacteria in the liquid bacterial agent is within the range of $1\times10^8$-$9\times10^8$ CFU·mL$^{-1}$.

4. A preparation method of the growth-promoting bacterial agent for soybeans according to claim 2, wherein the preparation method of the liquid bacterial agent comprises:
   S1. activating the DW1 strain: inoculating the DW1 strain into an LB slope medium, and culturing the DW1 strain at 25-30° C. for 18-30 h to obtain an activated DW1 strain; and
   S2. culturing the activated DW1 strain in a liquid medium: washing the DW1 strain on the LB slope medium with physiological saline, transferring the activated DW1 strain into 80-120 mL of the LB liquid medium with a volume ratio of 2-5%, and placing the LB liquid medium in a shaker at 25-30° C. and 120-180 r·min$^{-1}$ for shaking cultivation for 24-28 h to prepare the liquid bacterial agent.

5. An application method of the growth-promoting bacterial agent for soybeans according to claim 1, wherein the method comprises:
   performing seed soaking of soybeans with the growth-promoting bacterial agent; or
   performing coating of soybeans with the growth-promoting bacterial agent; or
   performing root watering of soybean with the growth-promoting bacterial agent.

* * * * *

SEQUENCE LISTING

```
Sequence total quantity: 1
SEQ ID NO: 1            moltype = DNA  length = 1424
FEATURE                 Location/Qualifiers
source                  1..1424
                        mol_type = genomic DNA
                        organism = Bacillus sp.
SEQUENCE: 1
atacatgcag tcgagcgaac tgattagaag cttgcttcta tgacgttagc ggcggacggg    60
tgagtaacac gtgggcaacc tgcctgtaag actgggataa cttcgggaaa ccgaagctaa   120
taccggatag gatcttctcc ttcatgggag atgattgaaa gatggtttcg gctatcactt   180
acagatgggc ccgcggtgca ttagctagtt ggtgaggtaa cggctcacca aggcaacgat   240
gcatagccga cctgagaggg tgatcggcca cactgggact gagacacggc ccagactcct   300
acgggaggca gcagtaggga atcttccgca atggacgaaa gtctgacgga gcaacgccgc   360
gtgagtgatg aaggctttcg ggtcgtaaaa ctctgttgtt agggaagaac aagtacgaga   420
gtaactgctc gtaccttgac ggtacctaac cagaaagcca cggctaacta cgtgccagca   480
gccgcggtaa tacgtaggtg gcaagcgtta tccggaatta ttgggcgtaa agcgcgcgca   540
ggcggtttct taagtctgat gtgaaagccc acggctcaac cgtggagggt cattggaaac   600
tggggaactt gagtgcagaa gagaaaagcg gaattccacg tgtagcggtg aaatgcgtag   660
agatgtggag gaacaccagt ggcgaaggcg gctttttggt ctgtaactga cgctgaggcg   720
cgaaagcgtg gggagcaaac aggattagat accctggtag tccacgccgt aaacgatgag   780
tgctaagtgt tagagggttt ccgccctttta gtgctgcagc taacgcatta agcactccgc   840
ctggggagta cggtcgcaag actgaaactc aaaggaattg acgggggccc gcacaagcgg   900
tggagcatgt ggtttaattc gaagcaacgc gaagaacctt accaggtctt gacatcctct   960
gacaactcta gagatagagc gttcccnttc ggggacaga gtgacaggtg gtgcatggtt  1020
gtcgtcagct cgtgtcgtga gatgttgggt taagtcccgc aacgagcgca acccttgatc  1080
ttagttgcca gcatttagtt gggcactcta aggtgactgc cggtgacaaa ccggaggaag  1140
gtggggatga cgtcaaatca tcatgcccct tatgacctgg gctacacacg tgctacaatg  1200
gatggtacaa agggctgcaa gaccgcgagg tcaagccaat cccataaaac cattctcagt  1260
tcggattgta ggctgcaact cgcctacatg aagctggaat cgctagtaat cgcggatcag  1320
catgccgcgg tgaatacgtt cccgggcctt gtacacaccg cccgtcacac cacgagagtt  1380
tgtaacaccc gaagtcggtg gagtaaccgt aaggagctag ccgc                   1424
```